United States Patent [19]

Gerber

[11] 4,083,249

[45] Apr. 11, 1978

[54] HYGROMETER

[75] Inventor: Hermann E. Gerber, Reston, Va.

[73] Assignee: The United States of America as represented by the Secretary of the Navy, Washington, D.C.

[21] Appl. No.: 759,935

[22] Filed: Jan. 17, 1977

[51] Int. Cl.² ............................................. G01N 25/68
[52] U.S. Cl. ................................. 73/336.5; 73/17 A
[58] Field of Search ............. 73/17 A, 29, 335, 336.5; 340/235

[56] References Cited

U.S. PATENT DOCUMENTS

| | | | |
|---|---|---|---|
| 2,415,776 | 2/1947 | Walton | 73/17 A |
| 2,492,768 | 12/1949 | Schaeffer | 73/335 |
| 3,166,928 | 1/1965 | Jackson | 73/17 |
| 3,269,185 | 8/1966 | Francisco | 73/336.5 |
| 3,388,863 | 6/1968 | Andersen et al. | 236/44 R |
| 3,465,591 | 9/1969 | Bachem et al. | 73/336.5 |
| 3,661,724 | 5/1972 | Strickler | 73/335 X |
| 3,664,192 | 5/1972 | Campbell et al. | 73/336.5 |

Primary Examiner—Richard C. Queisser
Assistant Examiner—John S. Appleman
Attorney, Agent, or Firm—R. S. Sciascia; Philip Schneider; Melvin L. Crane

[57] ABSTRACT

A supersaturation hygrometer formed by a thermo-optical servo system which responds to water vapor changes in the range just above and below water saturation. The system includes a hydrophobic metal chip on which monodisperse submicron salt particles act as centers of water condensation. A change in scattered light from the solution droplets on the chip drives an infrared source which heats the chip to keep the size of the droplets constant. The infrared power is related to the chip ambient temperature difference which is proportional to the ambient water vapor pressure.

11 Claims, 2 Drawing Figures

HYGROMETER

BACKGROUND OF THE INVENTION

This invention relates to hygrometers and more particularly to a hygrometer that will measure relative humidity just below and just above 100%.

Heretofore relative humidity (RH) devices have been able to make measurements in the range from 0 to about 95%; however, the prior art instruments rapidly loose their accuracy for RH values greater than 95% and some are destroyed at an RH of 100% due to their interaction with the water vapor. Such instruments include a dry substance-type in which the gain in weight due to water vapor is a measure of the relative humidity. Another type consists of a brightly polished surface which is cooled until vapor from the air begins to form on the surface and the temperature at which the vapor forms is a determining factor as to the relative humidity. Another type is the wet bulb-type. A further type includes a pointer connected to a slender axle about which a suitable material is wrapped which rotates the axle in either direction as the water vapor content in the air varies.

SUMMARY OF THE INVENTION

The device of this invention operates to determine relative humidity just below and just above 100%. Salt particles are placed on a hydrophobic-film-coated polished substrate. The salt particles act as controlled condensation sites on which liquid condenses to form solution droplets. The device is placed in the atmosphere which flows past the device parallel to the substrate, and moisture from the atmospheric flow is collected by the salt particles changing their size. A portion of the light from a source illuminating the substrate is scattered by the droplets. The amount of scattered light is indicative of the size of the droplets.

The operation of the device is controlled by a thermo-optical servo system which operates as follows: The scattered light from the droplets is compared to a reference light, the difference in the intensities of these lights is used to drive a heater which heats the substrate and thus shrinks the salt droplets thereby decreasing the scattered light, and the magnitude of the power to the heater, which causes the difference between the scattered and reference light intensities to vanish, is the measure of the ambient relative humidity.

DETAILED DESCRIPTION

Figure 1:
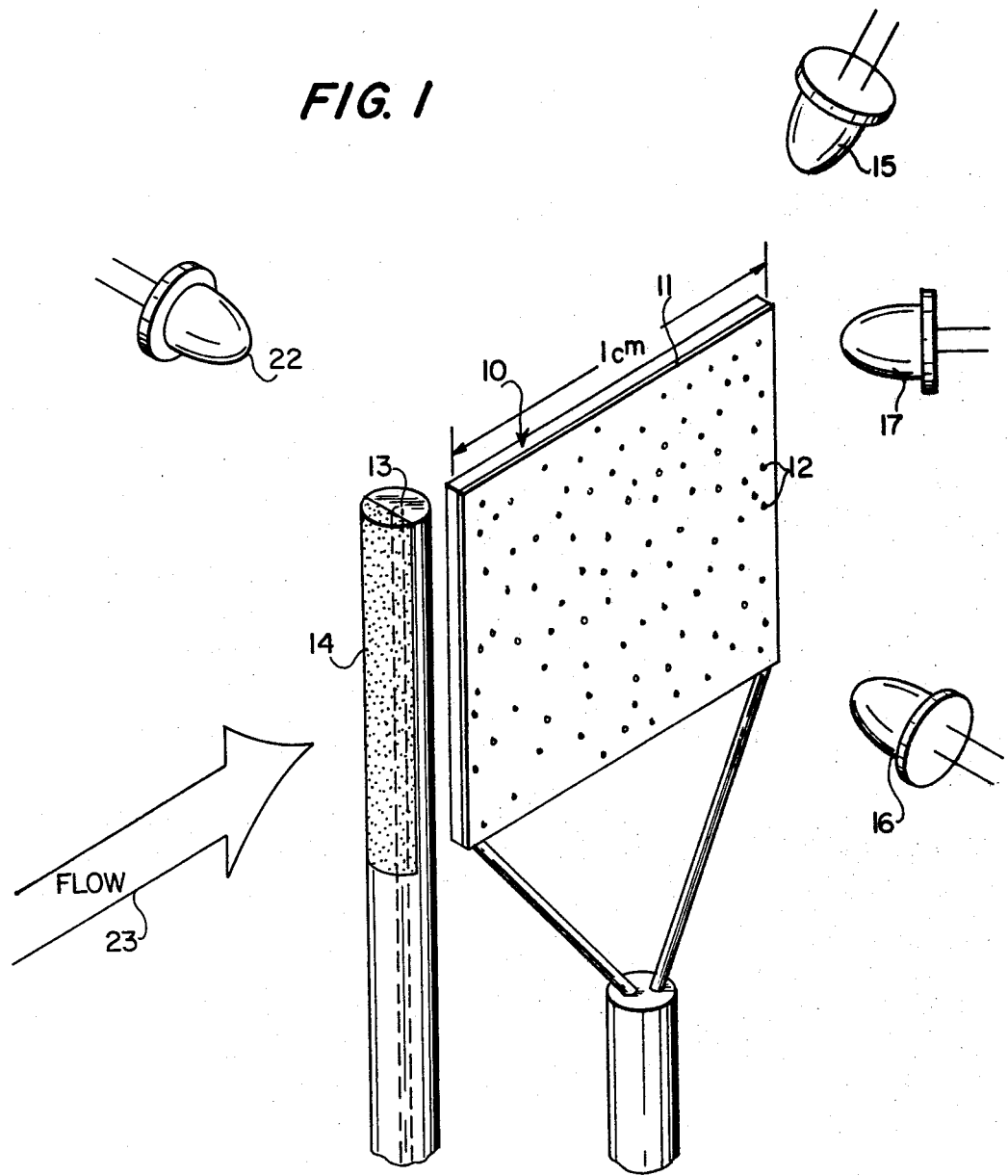
FIG. 1 illustrates the relationship between the elements of an embodiment of the invention.
Figure 2:
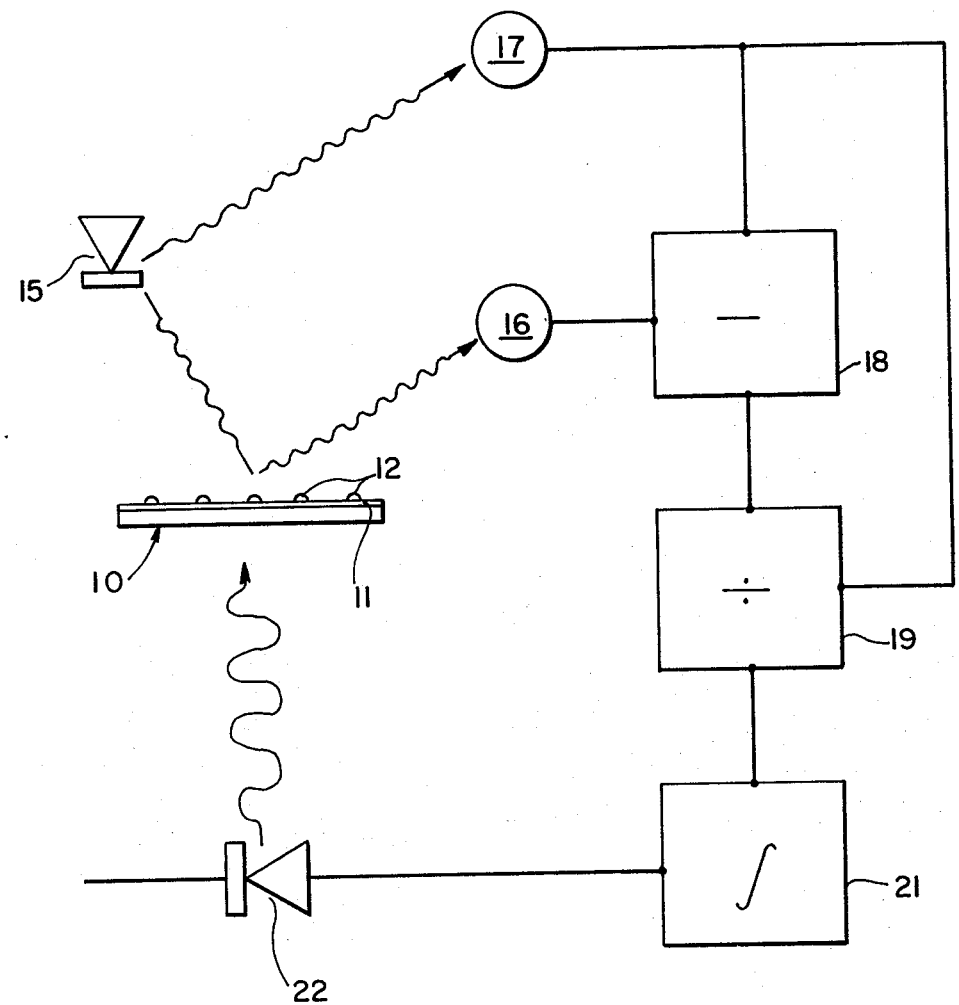
FIG. 2 illustrates the relationship of the elements in combination with the signal-processing apparatus.

FIGS. 1 and 2 illustrate a thermo-optical servo system including a thin chip or substrate 10 which may be made of a metal which is highly reflective on one side or perhaps polished to become highly reflective or of a material such as glass which may be coated with a surface which is highly reflective or polished to become highly reflective. The highly reflective surface is coated with a thin coating 11 of a hydrophobic film such as Dry-Film 88. A dispersion of monodisperse salt paticles 12 having a size of from about 0.1 to about 1.0 microns in diameter are placed on the reflective side of the substrate.

A water drop guard 13 having a leading edge 14 of a porous material, such as sintered metal or plastic or a membrane filter, which absorbs large drops of water is placed along one edge of the salt-covered substrate. The excess water absorbed by the porous material is removed by suction by a device which is omitted to simplify the drawing.

A light source, for example a light-emitting injection laser diode 15 such as manufactured by Laser Diodes, Inc., is secured relative to the salt-coated surface of the substrate so that light is directed toward the surface of the substrate at a shallow angle thereby illuminating the surface. A scattered-light detector 16, such as a hybrid photodiode MDA 438 manufactured by Meret Inc., measures the intensity of light scattered from the illuminated salt particles. A second light sensor 17, such as set forth above, is positioned to directly measure the full intensity of the light emitted by the light-emitting diode. The light detectors 16 and 17 convert the received light into electrical output signals which are electonically processed by a differencing circuit 18 and the difference output signal is directed to a dividing circuit 19. The output signal of the detector 17 is also directed to the dividing circuit where it is electronically divided into the difference signal. The output from the dividing circuit is integrated by an integrator circuit 21 whose output is directed to a heat source 22, such as the LED-56 infrared-radiation-emitting diode manufactured by General Electric Company. The infrared-emitting diode directs its output onto the back side of the salt-covered substrate to heat the substrate in accordance with the differentiated signal output received.

In carrying out the invention, the thin polished substrate is coated on its front side with the hydrophobic film to retard the condensation of liquid from a vapor with a relative humidity about 100% on portions of the substrate between the salt particles. The salt particles are deposited onto the hydrophobic film side of the substrate where they act as controlled condensation sites on which the liquid condenses to form solution droplets. The small particle size of the salt prevents uncontrolled growth of the solution droplets. The finished substrate is positioned in a small wind tunnel with the subtrate parallel to the direction of flow of the atmosphere through the wind tunnel with the water-drop guard extending along the leading edge of the substrate. The light source, detectors and infrared-emitting diode are all positioned relative to the substrate to carry out their functions.

In operation, the drop guard located along the leading edge of the substrate intercepts large atmospheric drops which may be entrained in the atmospheric flow passing through the tunnel and which could cause deterioration of the substrate and salt coating should they collide therewith. The drops so collected by the drop guard are removed by suction from below.

The salt particles collect water vapor from the atmosphere as the atmosphere flows past the substrate. The size of the resulting salt-solution droplets increases with increasing ambient relative humidity and decreases with decreasing humidity.

Measurement is accomplished by use of the thermo-optical-servo-system. Pulses of light produced by the laser diode are directed onto the salt-solution-droplet-covered surface of the substrate at a shallow angle. The light incident on the substrate is scattered by the salt-solution-droplets into a light detector and the intensity of the light is measured. This intensity depends upon the size of the salt-solution-droplets which are in turn dependent upon the amount of water vapor in the atmosphere. The larger the size of the salt-solution-droplets, the more the light is scattered. The more the light is scattered, the greater the output signal from the light detector. Also, pulses of light from the laser diode are directed toward a direct-measurement light sensor which measures the intensity of the emitted light. As mentioned earlier, the output from each light sensor is directed into a differencing circuit which produces an output signal proportional to the difference in the light intensity received by each sensor. The difference output signal is directed into a dividing circuit by which the difference output signal is divided by the output signal from the direct measurement sensor. The dividing circuit output signal is directed to an integrator circuit whose output is directed to the infrared diode heater. The difference, dividing and differential circuits are such that, if the output signal from the scattered-light sensor is larger than the output signal from the direct-light sensor, the infrared diode heater is activated to heat the substrate; The heater partially evaporates the salt-solution droplets which in turn reduces the intensity of the scattered light detected by the scattered-light sensor. The heater tends to evaporate the droplets back to their calibration size, i.e. their size for the 100% RH condition, It is important to note in this respect that prior to use of the system for measuring the relative humidity (RH) in existing and incipient clouds and fog, the output signals from the scattered-light sensor and the output of the direct-light sensor are adjusted to be identical at a calibration value of RH = 100% (this means that the intensity of the signal from the direct-light sensor must be reduced to equal that from the scattered light sensor). If the ambient RH increases over the calibration value, the solution droplets tend to grow thereby scattering more light. Since more light is scattered, an error signal will exist between the outputs of the two sensors which will activate the heater diode. The magnitude of the integrated power to the heater is the measure of the ambient relative humidity.

Relative humidities just below 100% may also be obtained by measuring the signal output of the scattered-light sensor by use of a separate readout channel. What is done here is simply to measure the magnitude of the difference signal rather than the power required to run the infrared-emitting source.

The material from which the substrate is made is not critical so long as it is a good heat conductor. It is important that one surface on the substrate be highly reflective.

The light source 15 is directed toward the surface of the substrate at a shallow angle to avoid scattering of the light by any near-by droplets in the volume of air which passes outwardly of the water guard and near the surface of the substrate. It has been determined that the shallow angle may be from 10° to 20°.

The materials, types of elements and/or equipment are all illustrative and any other suitable elements or equipment which will serve the same purpose may be used.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A hygrometer for measuring the relative humidity of an atmosphere comprising:
   a substrate with at least one optically highly reflective, hydrophobic surface;
   a plurality of closely spaced controlled water-condensation means arranged in planar form on said hydrophobic surface, said controlled water-condensation means acting to condense water vapor to form solution droplets at the locations of said controlled water-condensation means;
   light-emitting means for illuminating said controlled water-condensation means;
   scattered-light detecting means for detecting light scattered by said solution droplets at the locations of said controlled water-condensation means and for producing an output signal proportional to the intensity of the scattered light;
   direct-light detecting means for detecting the direct light from the light-emitting means and for producing an output signal proportional to the intensity of direct light;
   means for obtaining the difference between the output signals of said detecting means and for producing an output signal proportional to the difference;
   means for equalizing the direct and reflected-light output signals when the relative humidity of the atmosphere is 100%; and
   means for utilizing the difference signal to provide an indication of the corresponding relative humidity.

2. A hygrometer as in claim 1, wherein:
   said condensation means comprise monodisperse salt particles having a diameter in the approximate range of 0.1–1.0 micron.

3. A hygrometer as claimed in claim 2 which includes:
   a droplet guard located along one edge of said substrate.

4. A hygrometer as claimed in claim 2 wherein:
   said monodisperse salt particles are arranged in planar form and dispersed such that their size is a small fraction of the distance between the particles whereby said salt particles form condensation sites.

5. A hygrometer as in claim 1, further comprising:
   means, connected to receive said difference signal, for emitting infrared radiation which is directed at said substrate so as to reduce the size of said water droplets until the difference signal reaches zero,
   said means for utilizing the difference signal comprising means to measure the power which the difference signal provided to said infrared-radiation emitting means.

6. A hygrometer as claimed in claim 1, wherein
   said light-emitting means illuminates said controlled water condensation means at a shallow angle to the plane that the controlled water-condensation means form.

7. A hydrometer as claimed in claim 6 which includes:
   a droplet guard located along one edge of said substrate.

8. A hygrometer as claimed in claim 1 in which:
   said substrate is thin and highly polished on the side upon which said condensation sites are deposited, and
   made of a good heat-conductive material.

9. A hygrometer as claimed in claim 8 which includes:

a droplet guard located along one edge of said substrate.

10. A hygrometer as claimed in claim 1 which includes:
a droplet guard located along one edge of said plurality of closely spaced water condensation means arranged in planar form.

11. A hygrometer as claimed in claim 10 wherein:
said droplet guard is made of a porous sintered material which intercepts large atmospheric drops which are entrained in the atmospheric flow passing said droplet guard.

* * * * *